(12) United States Patent
Schweikert

(10) Patent No.: US 7,993,309 B2
(45) Date of Patent: Aug. 9, 2011

(54) SCRUBBER FOR MEDICAL DEVICE CLEANER

(75) Inventor: Timothy Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 12/760,829

(22) Filed: Apr. 15, 2010

(65) Prior Publication Data

US 2010/0192975 A1 Aug. 5, 2010

Related U.S. Application Data

(62) Division of application No. 11/180,142, filed on Jul. 13, 2005, now Pat. No. 7,857,793.

(51) Int. Cl.
*A61M 25/00* (2006.01)

(52) U.S. Cl. .......... 604/267; 15/104.09; 15/104.096

(58) Field of Classification Search .......... 15/104.09, 15/104.096; 134/6; 604/174–180, 267, 284, 604/533

See application file for complete search history.

(56) References Cited

U.S. PATENT DOCUMENTS

| | | |
|---|---|---|
| 3,971,376 A | 7/1976 | Wichterle |
| 4,301,567 A | 11/1981 | Tucker |
| 4,432,764 A | 2/1984 | Lopez |
| 4,439,884 A | 4/1984 | Giorni |
| 4,440,207 A | 4/1984 | Genatempo et al. |
| 4,624,664 A | 11/1986 | Peluso et al. |
| 5,048,547 A | 9/1991 | Walker |
| 5,375,589 A | 12/1994 | Bhatta |
| 5,471,706 A * | 12/1995 | Wallock et al. .......... 15/302 |
| 5,554,135 A | 9/1996 | Menyhay |
| 5,567,495 A | 10/1996 | Modak et al. |
| 5,792,120 A | 8/1998 | Menyhay |
| 5,795,339 A | 8/1998 | Erskine |
| 6,045,539 A | 4/2000 | Menyhay |
| 6,086,275 A * | 7/2000 | King .......... 401/11 |
| 6,269,512 B1 * | 8/2001 | Thomson et al. .......... 15/104.92 |

(Continued)

FOREIGN PATENT DOCUMENTS

WO 87/00441 A1 1/1987

OTHER PUBLICATIONS

European Search Report dated Dec. 23, 2010; European Application No. 05770621.0-2320 (7 pages).

(Continued)

*Primary Examiner* — Nicholas D Lucchesi
*Assistant Examiner* — Gerald Landry, II
(74) *Attorney, Agent, or Firm* — Anton P. Ness; Fox Rothschild LLP

(57) ABSTRACT

A luer cleaner (100) including a generally hollow body (112) having an open first end (104), a closed second end (106), and a longitudinal axis extending therethrough between the first end and the second end. The first end (104) is sized to receive therein a luer connector (190) proximal end and includes a plurality of bristles (134) extending generally toward the longitudinal axis sufficiently to engage the outer surfaces of the luer proximal end disposed therein. The second end comprises a compressible reservoir (166) containing a fluid (168), wherein, when the second end is compressed, the fluid is transmitted from the reservoir toward the first end through passageways to wet the luer proximal end. A method for cleaning luer connectors is also disclosed.

15 Claims, 6 Drawing Sheets

U.S. PATENT DOCUMENTS

| | | | |
|---|---|---|---|
| 6,450,810 B1 | 9/2002 | Fisher et al. | |
| 6,602,219 B2 | 8/2003 | Madsen et al. | |
| 6,673,031 B2 | 1/2004 | Mark | |
| 6,813,797 B1 | 11/2004 | Kadinger | |
| 6,813,798 B2 * | 11/2004 | Moga | 15/104.93 |
| 6,983,508 B2 * | 1/2006 | Saurer | 15/104.04 |
| RE39,499 E | 2/2007 | Racz | |
| 7,198,611 B2 | 4/2007 | Connell et al. | |
| 2001/0016962 A1 | 8/2001 | Moore et al. | |
| 2002/0092524 A1 | 7/2002 | Lockhart et al. | |
| 2003/0060746 A1 | 3/2003 | Mark | |
| 2003/0060781 A1 | 3/2003 | Mogensen et al. | |
| 2004/0021000 A1 | 2/2004 | Denisov | |
| 2004/0138612 A1 | 7/2004 | Shermer et al. | |
| 2005/0124970 A1 | 6/2005 | Kunin et al. | |
| 2005/0147525 A1 | 7/2005 | Bousquet | |

OTHER PUBLICATIONS

International Search Report, PCT/US05/24796, dated Sep. 5, 2006 (2 pages).

Written Opinion of International Searching Authority, PCT/US05/24796, dated Sep. 5, 2006 (3 pages).

Office Action dated Jul. 26, 2010; Japanese Application No. 2007-521593 (4 pages).

* cited by examiner

SCRUBBER FOR MEDICAL DEVICE CLEANER

CROSS-REFERENCE TO RELATED APPLICATION

This is a Division application that relates to and claims priority from U.S. patent application Ser. No. 11/180,142 filed Jul. 13, 2005 which in turn claims priority from Provisional U.S. Patent Application Ser. No. 60/587,790 filed Jul. 14, 2004.

FIELD OF THE INVENTION

The present invention relates to medical device, and more particularly to an apparatus for cleaning a luer connector that is attached to a catheter assembly implanted on a patient.

BACKGROUND OF THE INVENTION

In catheter assemblies such as are used in hemodialysis, proximal ends of the catheters are terminated in luer connectors that are disposed outside of the patient, and the luer connectors enable easy and rapid connection to respective fluid lines of the hemodialysis apparatus in a manner permitting easy and rapid disconnect. Of course, when unconnected to the fluid lines, the ends of the luer connectors are exposed to debris and contamination and they require cleaning and decontamination prior to each connection.

SUMMARY OF THE INVENTION

The present invention is a cleaner for a medical device such as a luer connector, or luer, that includes a generally hollow body having an open first end, a closed second end, and a longitudinal axis extending therethrough between the first end and the second end. The first end is sized to receive therein the proximal end of the luer connector, and includes a scrubber to engage the luer connector disposed therein. The second end comprises a compressible reservoir containing a fluid, wherein, when the second end is compressed, the fluid is transmitted from the reservoir toward the first end. When the luer cleaner is inserted over the proximal end of the luer connector and preferably is rotated reciprocally several times about the luer's axis, the scrubber engages and mildly scrubs the outer surfaces of the luer's proximal end, including the male connector threads, to dislodge debris, and the fluid washes and thus cleans and decontaminates the luer connector end when the luer cleaner is removed from the luer connector.

The present invention includes a scrubber having a peripheral body and a plurality of flexible generally pointed projections extending radially inwardly therefrom, to engage outer surfaces of a medical device inserted therethrough. Even further, the present invention includes a cleaner for a medical device including a hollow body containing one or more scrubbers each having flexible projections extending radially inwardly to engage and scrub outer surfaces of a medical device inserted into the hollow body.

Other embodiments of the luer cleaner provide a frangible capsule within the reservoir at the second luer cleaner end that contains the fluid and that expresses the fluid when crushed; and provide a pair of frangible capsules within the reservoir, that contain the fluid and together express the fluid.

BRIEF DESCRIPTION OF THE DRAWINGS

The accompanying drawings, which are incorporated herein and constitute part of this specification, illustrate the presently preferred embodiments of the invention, and together with the general description given above and the detailed description given below, serve to explain the features of the invention. In the drawings.

DETAILED DESCRIPTION OF THE INVENTION

Figure 1:
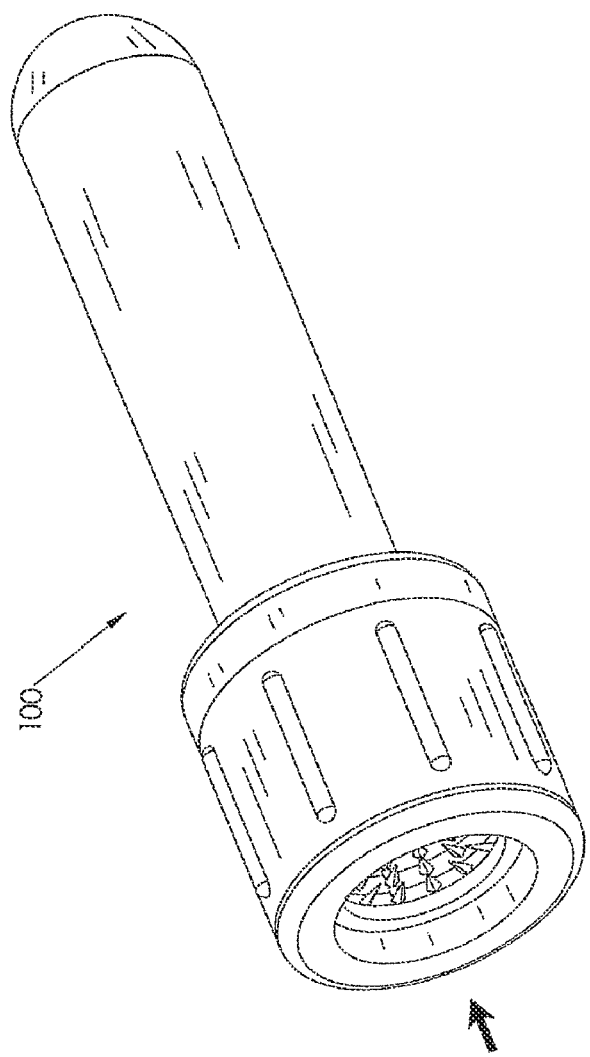
FIG. 1 is a perspective view of a luer cleaner according to a first preferred embodiment of the present invention, with a luer being inserted into the luer cleaner.
Figure 1:
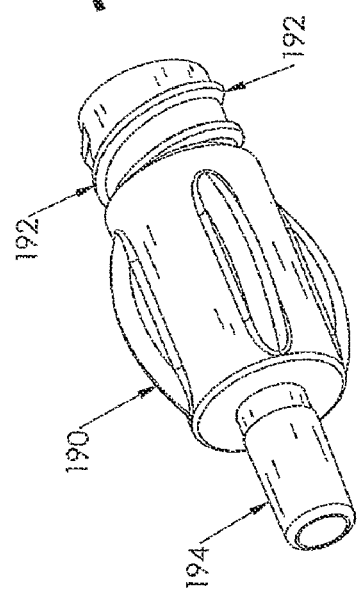

In the drawings, like numerals indicate like elements throughout. Certain terminology is used herein for convenience only and is not to be taken as a limitation on the present invention. The words "proximal" and "distal" refer to directions away from and closer to, respectively, the inserted portion of the catheter assembly within the patient's vasculature. The terminology includes words specifically mentioned, derivatives thereof, and words of similar import. The following describes preferred embodiments of the invention. However, it should be understood based on this disclosure that the invention is not limited by the preferred embodiments described herein.

Referring now to FIG. 1, a luer cleaner 100 according to a first embodiment of the present invention is shown. The luer cleaner 100 is insertable over the proximal end of a luer connector 190 and rotatable axially about the luer. Luer connector, or luer, 190 is preferably connected to a medical device, such as a hemodialysis catheter 194. The proximal end of luer 190 includes male threads 192 that are used to secure luer 190 to a second medical device (e.g., a hemodialysis apparatus) having fluid lines each terminating in a corresponding luer connector that incorporates internal female threads. Prior to connection of the luer 190 with the second medical device, the proximal end of luer 190 is inserted into an open end of the luer cleaner 100. As the luer cleaner 100 is rotated about the luer 190, antiseptic fluid contained in the luer cleaner 100 is forced from a reservoir in the luer cleaner 100 such as by manually applied pressure, over the luer 190, to clean debris and other contaminants that may be present on or around the luer threads 192. Also shown, along with FIGS. 2 and 3, is a body 160 defining a reservoir 166 for a fluid 168.

Figure 2:
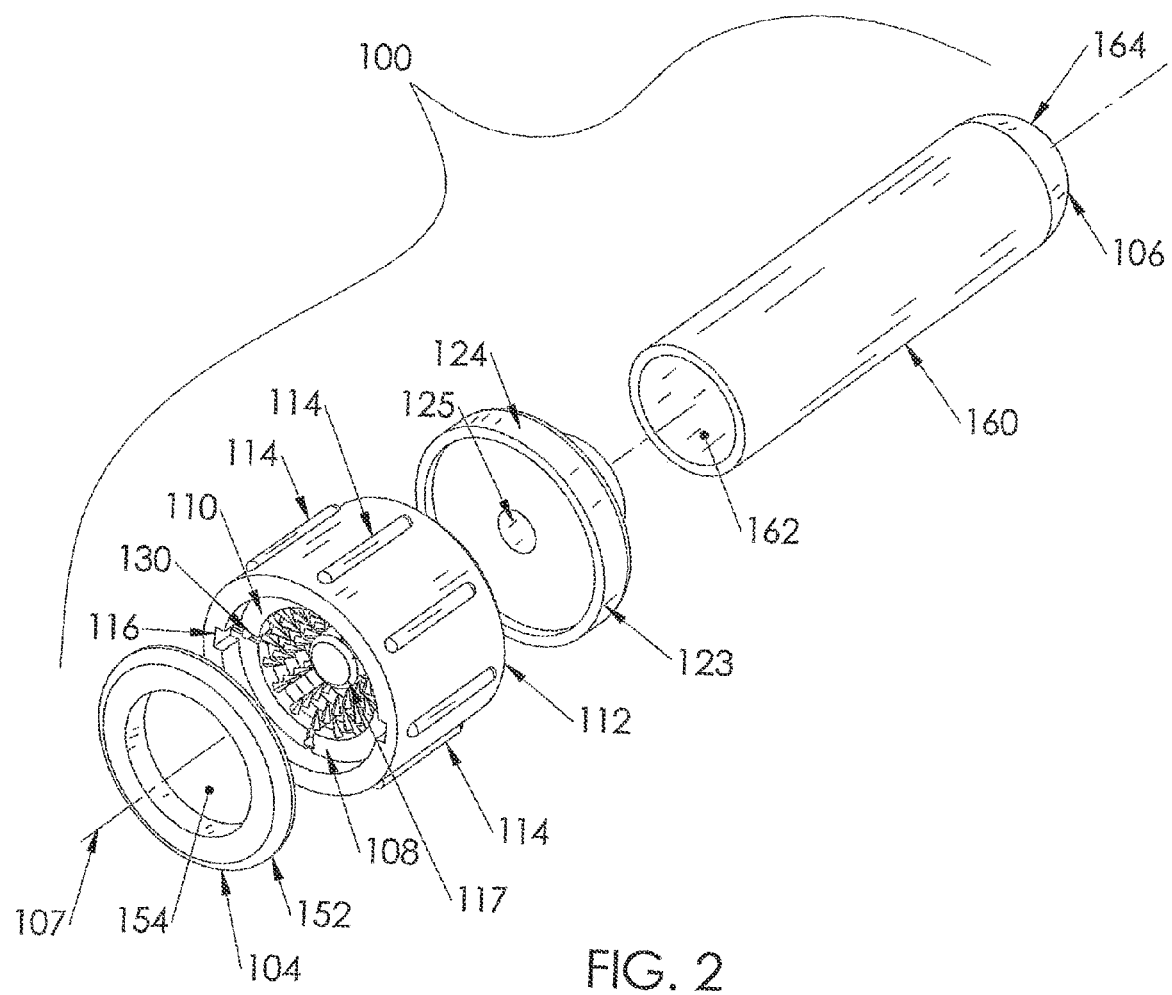
FIG. 2 is an exploded view of the luer cleaner shown in FIG. 1.
Figure 3:
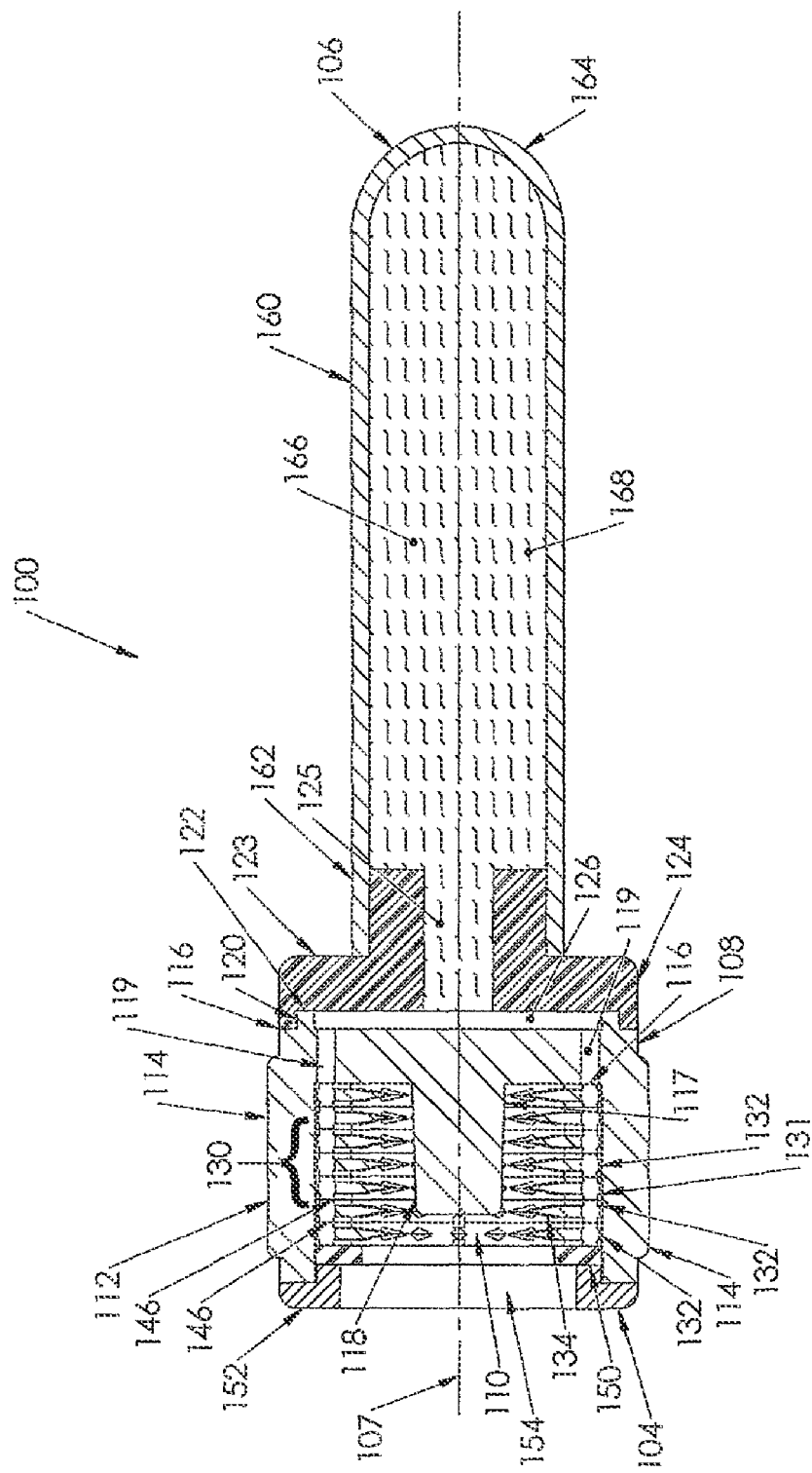
FIG. 3 is a sectional view of the luer cleaner shown in FIG. 1.

Referring now to FIGS. 2 and 3, the luer cleaner 100 includes an open end 104, a closed end 106, and a longitudinal axis 107 extending therethrough between the open end 104 and the closed end 106. The open end 104 includes a generally tubular body 108 having a longitudinal passage 110 that extends toward the closed end 106. Preferably, the body 108 is constructed from polyvinyl chloride or some other suitable biocompatible material. The body 108 includes an exterior portion 112 that may optionally include a plurality of gripping ribs 114 extending therefrom, away from the longitudinal axis 107. The gripping ribs 114 allow a user to grip the body 108 during use of the cleaner 100. The interior of the body 108 includes at least one, and preferably two, diametrically opposed alignment notches 116 that extend from the longitudinal passage 110 away from the longitudinal axis 107.

The body 108 further includes a guide member 117 that extends partially into the longitudinal passage 110 along the longitudinal axis 107 toward the open end 104. The guide member 117 preferably includes a male luer taper 118 to engage a female luer connection on the luer 190. The guide member 117 prevents fluid from entering the catheter 194 through the interior of the luer 190 after the fluid has been forced into the longitudinal passage 110 from the reservoir. The guide member 117 is preferably integrally molded with the body 108, as seen in the cross-section view of FIG. 3.

At least one and preferably four passages 119 are disposed within the body 108 between the exterior portion 112 of the body 108 and the guide member 117 (although only two passages 119 are shown in FIG. 3). The passages 119 are preferably parallel to the longitudinal axis 107 and each passage 119 is disposed ninety degrees apart from each adjacent passage 119.

The body 108 also includes an annular flange 120 that extends from the body 108, away from the open end 104 of the luer cleaner 100. The flange 120 extends outwardly of the passages 119, with a lip 122 being formed between the flange 120 and the exterior portion 112 of the body 108.

A tubular collar 123, having an approximately "T-shaped" cross section, is fixedly connected to the body 108, distal from the open end 104 of the luer connector 100. The collar 123 includes a corresponding lip 124 that extends circumferentially therearound and that is sized to surround and engage with the flange 120 of the body 108, as is seen in FIG. 3. The connection between the collar 123 and the body 108 may be an interference fit, a threaded connection, an adhesive-based connection, or some other suitable connection known to those skilled in the art.

The collar 123 also includes a connecting passage 125 that extends through the collar 123, generally along the longitudinal axis 107, with the connecting passage having a small diameter, as seen in FIG. 3. When the collar 123 and the body 108 are engaged with each other, a generally circular throughway 126 is formed between the body 108 and the collar 123 that provides fluid communication between the connecting passage 125 and the very small diameter passages 119 in the body 108.

Figure 5:
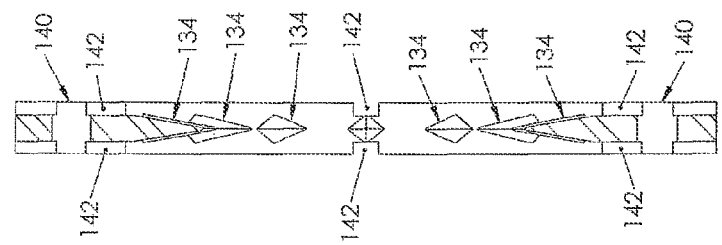
FIG. 5 is a sectional view of the scrubber disc of FIG. 4, taken along line 5-5 of FIG. 4.
Figure 4:
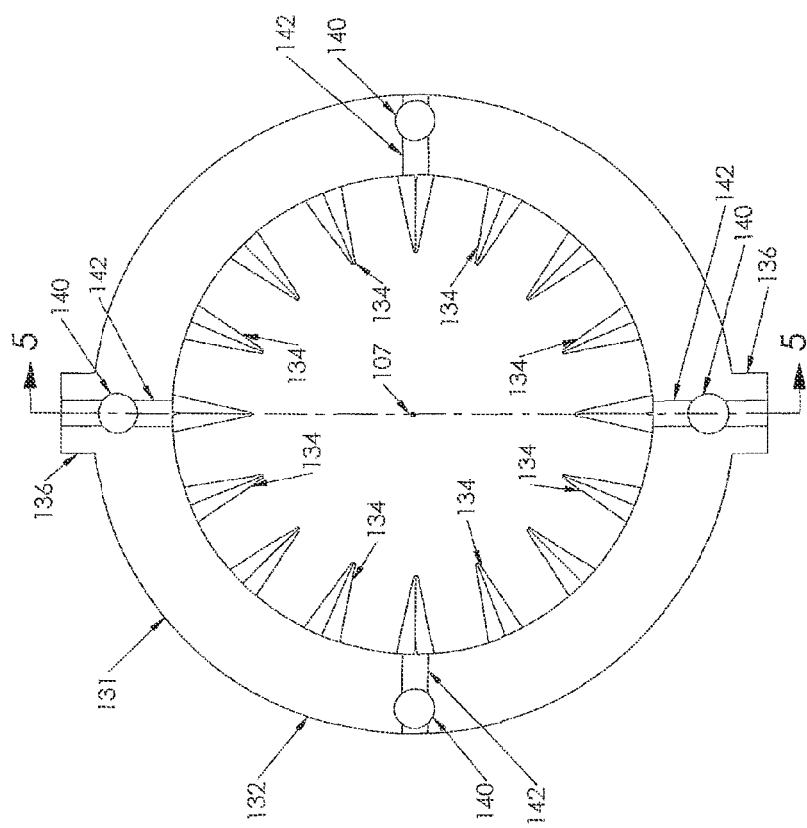
FIG. 4 is an enlarged front view of a scrubber disc shown inside the luer cleaner.

A scrubber 130 is disposed within the longitudinal passage 110 and is preferably constructed from at least one, and preferably a plurality, of scrubber discs 131. Details of a scrubber disc 131 are shown in FIGS. 4 and 5; each scrubber disc 131 includes an annular ring or peripheral portion 132 having a central aperture therethrough, with each ring 132 having a plurality of flexible generally pointed projections or scrubber bristles 134 extending radially inwardly therefrom into the central aperture toward the longitudinal axis 107. It may be seen from FIGS. 4 and 5 that scrubber disc 131 is so shaped that it may be of unitary construction. It may also be seen that the projections 134 are spaced apart from each other about the peripheral portion 132 and are narrow and diamond-shaped in cross-section, and that the thickness of each projection measured axially, is less than the thickness of the peripheral portion 132; as a result, flexibility is facilitated axially and side-to-side. Preferably, the rings 132 and flexible projections 134 are constructed from polypropylene or some other suitable biocompatible material, and are non-abrasive to mildly scrub the luer surfaces. The flexible projections 134 extend sufficiently far toward the center of each ring 132 so as to engage the luer threads of the luer when the luer is inserted into the luer cleaner 100.

Preferably, the ring 132 for each scrubber disc 131 includes at least one, and preferably two diametrically opposed, alignment posts 136 that extend from the outer perimeter of the ring 132 away from the center of the ring 132. Each post 136 is sized and shaped to fit into a respective alignment notch 116 cut into the body 108. Each post 136 engages the alignment notch 116 in a generally tight, frictional fit so that each ring 132 remains within the longitudinal passage 110 after insertion thereinto.

Each ring 132 also includes at least one, and preferably, a plurality of through-passages 140 that allow fluid to pass from one side of each ring 132 to an opposing side of each ring 132. Four through-passages 140 are preferred, as shown in FIG. 4, with each through-passage 140 being disposed at ninety-degree spacings from each adjacent through-passage 140, although those skilled in the art will recognize that more or less than four through-passages 140 may be used. However, it is preferred that each through-passage 140 fluidly communicates with a passage 119 in the body 108, so that fluid communication exists between all of the passages 140 and the connecting passage 125.

Further, a plurality of radially extending channels 142 extends along transverse surfaces of each ring 132 from the outer perimeter of the ring 132 to the inner diameter of the ring 132, with each channel 142 fluidly communicating with a through-passage 140. As can be discerned from FIGS. 4 and 5, four channels 142 are disposed at ninety-degree spacings apart from each adjacent channel 142, with channels 142 disposed on either side of each ring 132, although those skilled in the art will recognize that, for each through-passage 140, a channel 142 is preferably disposed on either face of the ring 132.

With a plurality of rings 132 disposed adjacent one another, as shown in FIG. 3, the radially extending channels in adjacent rings 132 form radial passages 146 that provide fluid communication between each through-passage 140 and the longitudinal passage 110 to allow fluid to be transmitted through the radial passages 146 to the longitudinal passage 110. Fluid communication is now present between the longitudinal passage 110 and the connector passage 125.

Again referring to FIG. 3, sealing ring 150 is disposed between the array of rings 132 and the open end 104 of the luer cleaner 100. The sealing ring 150 preferably has an internal diameter that is approximately the same as the external diameter of the luer 190 (see FIG. 1) to prevent fluid forced manually from the reservoir 168 within bulbous body 160 and into the longitudinal passage 110, from flowing out of the luer cleaner 100 between the luer and the body 108 of the cleaner 100. The sealing ring 150 is preferably constructed from KRATON™ or other suitable, flexible material, so that the sealing ring 150 generally provides a seal around the luer when the luer is inserted into the luer cleaner 100.

A cap 152 is disposed on the open end 104 of the luer cleaner 100 to retain the sealing ring 150 and the array of scrubber rings 132 within the luer cleaner 100. The cap 152 is preferably annular, with a generally circular central opening 154 that is sized to allow the luer to be inserted therethrough. The cap 152 is preferably fixedly connected to the body 108, such as with an adhesive, although those skilled in the art will recognize that the cap 152 may be retained by other methods, such as by interference fit, or a threaded connection.

The closed end 106 of the luer cleaner 100 includes a generally bulbous body 160 constructed from KRATON™, 1064 PVC, or some other suitable, compressible material. The body 160 includes an open end 162 that is fixedly and sealingly connected to the collar 123 and a closed end 164 disposed away from the open end 162. The interior of the bulbous body 160 defines a compressible reservoir 166. A fluid 168 is disposed within the reservoir 166 such that the reservoir 166 fluidly communicates with the longitudinal passage 110 of the generally tubular body 108 through the connecting passage 125, the circular throughway 126, the passages 119, the through-passages 140, and the radial passages 146.

Preferably, the fluid 168 is a fluid having antiseptic properties, such as alcohol. More preferably, the fluid 168 is sufficiently viscous to remain in the reservoir 166 in the absence of a compressive force on the body 160 of the reservoir 166, considering the small diameter of connecting passage 125. Such a preferred fluid 168 is isopropyl alcohol in a polymer suspension, such as polyvinyl alcohol, sold commercially by GOJO Industries as PURELL®, although those skilled in the art will recognize that other fluids, including, but not limited to, povodine iodine or hydrogen peroxide, or any combination thereof, may be used instead.

In use, and referring to FIGS. 1 and 3, the luer 190, such as on a proximal end of a catheter 194, is inserted into the open end 104 of the luer cleaner 100. The sealing ring 150 engages the external portion of the luer 190, restricting fluid 166 from being forced out of the open end 104 of the luer cleaner 100.

After the luer 190 is fully inserted into the open end 104 of the luer cleaner 100, the bulbous body 160 is then compressed, forcing the fluid 168 in the reservoir 166 from the reservoir 166 and eventually into the longitudinal passage 110 of the generally tubular body 108 by way of being forced through the connecting passage 125, the circular throughway 126, the passages 119, the through-passages 140, and the radial passages 146, to the longitudinal passage 110 and thus to the exterior of the luer 190. The luer 190 is rotated about the longitudinal axis 107 of the luer cleaner 100, in a preferably back-and-forth motion, so that the bristles 134 on the scrubber discs 131, in conjunction with the fluid 168, clean contaminants from the exterior of the luer 190, including the luer threads 192. After several seconds of scrubbing, the luer is removed from the luer cleaner 100, and the luer cleaner 100 may be discarded. Luer 190 is now disinfected and may be connected to an external medical device.

Figure 6:
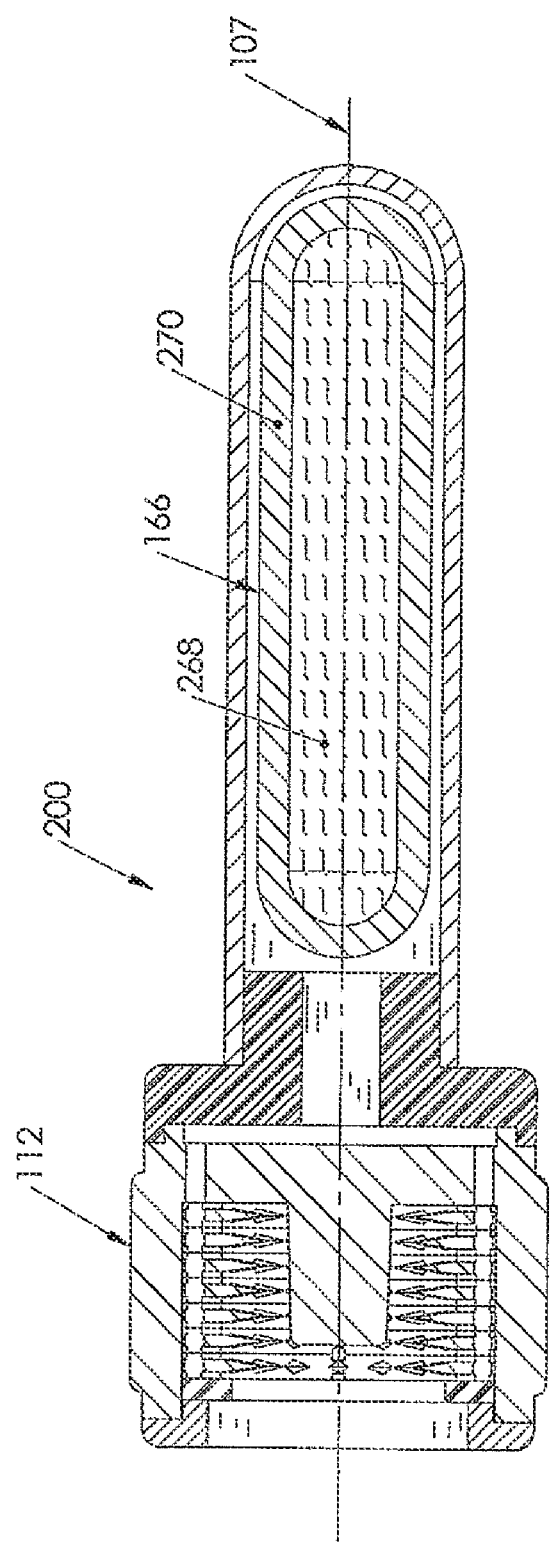
FIGS. 6 and 7 are sectional views of luer cleaners according to second and third embodiments of the present invention.

In an alternate embodiment of a luer cleaner 200, shown in FIG. 6, a fluid 268 may be retained in a frangible container 270 disposed within the reservoir 166. The fluid 268 may be significantly less viscous than the fluid 168 described above with respect to the luer cleaner 100 (FIG. 1). The frangible container 270 prevents the fluid 268 from flowing out of the reservoir 166 prior to use.

To use the luer cleaner 200, the luer is inserted into the open end 104 as described above with respect to the luer cleaner 100. The user compresses the reservoir 166 toward the longitudinal axis 107, breaking the frangible container 270, and allowing the fluid 268 to flow from the reservoir 166 and to the longitudinal passage 110 as described above with respect to the luer cleaner 100.

The frangible container 270 may be constructed from a material that is easily broken open under compression. The fluid 268 may be the same as the fluid 168 described above, or the fluid 268 may be a less viscous fluid, such as, for example, isopropyl alcohol without any suspension.

Figure 7:
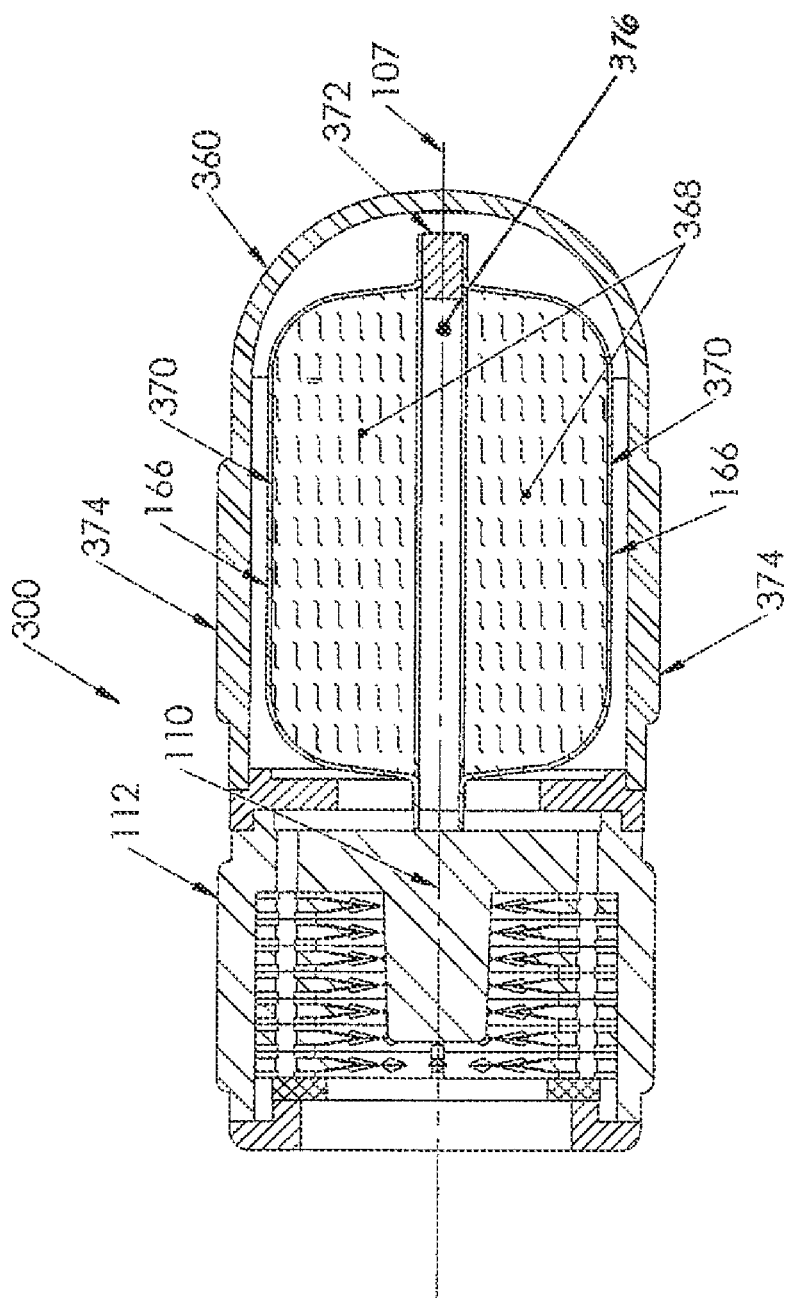

In FIG. 7, a third embodiment of luer cleaner 300 is shown. A pair of frangible containers 370 are secured to opposite sides of a tab 372, each containing quantities of fluid 368 that will be expressed into and forwardly through channel 376 of tab 372, as with the other luer cleaner embodiments. Luer cleaner 300 preferably provides visible indicators such as raised areas 374 on opposed outside surfaces of closed end 360 associated with respective ones of frangible containers 370, to enable the user to compress those indicated surfaces toward each other to crush the frangible containers 370 against tab 372, thus opening them for fluid 368 to enter tab channel 376 and forwardly into passageways of the luer cleaner open end.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A scrubber for cleaning a medical article, comprising: a generally flat, disc-shaped body having a central aperture therethrough defining an axis orthogonal to the body and having a peripheral portion surrounding the central aperture inwardly from which extends an array of projections each concluding generally in a point within the central aperture, wherein the projections are flexible, such that a medical article inserted through the body is engaged by the points of at least some of the projections so that when the medical article and the body are moved relative to each other, the points engage frictionally the outer surfaces of the medical article thus scrubbing same in a nonabrasive way.

2. The scrubber of claim 1, wherein the scrubber is of polypropylene material.

3. The scrubber of claim 1, wherein the disc-shaped body includes at least one axially extending peripheral opening through the peripheral portion.

4. The scrubber of claim 1, wherein transverse surfaces of the peripheral portion comprise at least one channel each extending radially inwardly from a respective at least one peripheral opening, for communicating cleaning fluid from the at least one opening radially inwardly to wet the flexible projections.

5. The scrubber of claim 1, wherein the array of flexible projections is planar.

6. A scrubber assembly comprising a plurality of disc-shaped bodies of claim 1 adjacent to each other and arranged such that their axes coincide.

7. The scrubber assembly of claim 6, wherein each disc-shaped body includes one planar array of flexible projections.

8. The scrubber assembly of claim 6, wherein each disc-shaped body has a peripheral portion that includes at least one axially extending peripheral opening therethrough, and the axially extending peripheral openings of the disc-shaped bodies are axially aligned.

9. The scrubber assembly of claim 6, wherein each disc-shaped body is of unitary construction.

10. The scrubber assembly of claim 6, wherein the flexible projections are spaced apart from each other about the peripheral portion of each disc-shaped body.

11. The scrubber assembly of claim 6, wherein each peripheral portion has a thickness measured axially, and each flexible projection has a thickness measured axially that is less than the thickness of the peripheral portion.

12. The scrubber of claim 1, wherein the disc-shaped body is of unitary construction.

13. The scrubber of claim 1, wherein the flexible projections are spaced apart from each other about the peripheral portion.

14. The scrubber of claim 1, wherein each peripheral portion has a thickness measured axially, and each flexible projection has a thickness measured axially that is less than the thickness of the peripheral portion.

15. The scrubber of claim 1, wherein each flexible projection is narrow and diamond-shaped in cross-section.

* * * * *